United States Patent [19]

Vaillancourt

[11] Patent Number: 5,059,174
[45] Date of Patent: Oct. 22, 1991

[54] FLUID INFUSION DELIVERY SYSTEM

[76] Inventor: Vincent L. Vaillancourt, 14 Bunyan Dr., Livingston, N.J. 07039

[21] Appl. No.: 572,696

[22] Filed: Aug. 23, 1990

[51] Int. Cl.5 .............................................. A61M 37/00
[52] U.S. Cl. ...................................... 604/82; 604/131; 128/DIG. 12
[58] Field of Search ................. 604/82, 131, 134, 135, 604/154, 151; 128/DIG. 12

[56] References Cited

U.S. PATENT DOCUMENTS 4,298,000  11/1981  Thill et al. .......................... 604/135
4,755,172  7/1988  Baldwin .............................. 604/131
4,785,799  11/1988  Schoon et al. .............. 128/DIG. 12
4,842,576  6/1989  Lysaght et al. .................. 604/131 X Primary Examiner—John D. Yasko
Attorney, Agent, or Firm—Kenyon & Kenyon

[57] ABSTRACT

The pump of the infusion delivery system delivers fluid at a positive pressure. A restrictor is provided in the line to the IV catheter in order to maintain a flow rate at the catheter outlet in a range of from 0.1 to 5 milliliters per hour. The small amount of fluid infused is sufficient to maintain the vein open without backup of blood.

15 Claims, 2 Drawing Sheets

FLUID INFUSION DELIVERY SYSTEM

This invention relates to a fluid infusion delivery system. More particularly, this invention relates to a fluid delivery apparatus and method of infusing fluid into a vein.

As is known, various techniques have been used for infusing medication, drugs and the like into a patient from time to time, for example using a procedure often known as SASH. This procedure is used where a patient is provided with an indwelling catheter having an intermittent injection port or cap which permits a drug delivery device to be removed in order to permit the patient to be ambulatory. The SASH procedure consists generally of filling a needle syringe with saline solution and injecting the syringe through the cap in order to flush out any Heparin present in the indwelling catheter. In this respect, Heparin is usually present in order to prevent blood clotting in the catheter and injection port (cap). After the Heparin has been cleared, the desired drug is infused and thereafter, a second injection of saline solution is used to clear the line of all drugs. This, in turn, is followed by an infusion of Heparin in order to keep the line patent prior to reinjection of the drug.

In order to avoid the need for the SASH procedure, it has been known to provide an ambulatory disposable infusion delivery system as described in U.S. Pat. No. 4,867,743. As described, such a system employs, inter alia, a small infusion device to feed a small continuous flow of physiological saline solution into a catheter placed in a patient. As described, this continually infused solution prevents occluding of the catheter and, as no Heparin is required, an added drug may be injected into the indwelling catheter in the desired amount and at the desired time. The system may also employ a restrictor in the fluid line so that the flow rate can be predicted for a given fluid.

Other types of ambulatory disposable infusion delivery systems have also been known, such as described in U.S. Pat. No. 4,813,937 which employ a housing with a piston movable under the force of a stretched elastomeric member and a restrictor in a delivery line in order to deliver medication from the housing in a controlled amount. After delivery of the medication, the emptied housing is usually removed and disposed of while a fresh housing filled with medication, for example from two to sixty cubic centimeters, is put in place.

In cases where infusion pumps which are not ambulatory are used in combination with IV line sets or where an IV line set with a gravity feed is used of itself, it has to keep a line open (normally referred to as KVO-keep vein open) by infusing 15 to 25 milliliters per hour of fluid thorugh the line into a patient. This quantity of fluid is used because, generally, the infusion pump is intermittent in operation thereby requiring a large quantity of fluid to overcome a period when the pump is shut down and blood is diffusing back up into the IV set. When a gravity set is used, it has been extremely difficult to maintain low volume drip rates without having periods of interruption when there is no flow. Hence, the KVO rate is approximately 20 to 25 milliliters per hour.

It has been found in one study involving an AIDS patient that a pump operating in the normal mode at a rate of 60 milliliters per hour (that is, delivering approximately 1 milliliter per minute over approximately a 10 second period with a rest period of 50 seconds) that after approximately 6 hours, the AIDS virus was detected four feet up the IV Administration Set connected between the patient and the pump. This appeared to be due entirely to diffusion which more than compensated for the flow rate and washing effect when flow was in progress.

Accordingly, it is an object of the invention to maintain a positive pressure at all times at the opening of a catheter into a vein.

It is another object of the invention to prevent diffusion of blood into a catheter and infusion line of an ambulatory disposable infusion delivery system.

Briefly, the invention provides a fluid delivery apparatus for a fluid infusion delivery system which is comprised of a fluid delivery line, a pump for continuously delivering fluid under a positive pressure into the delivery line and a restrictor in the delivery line for producing a continuous low flow rate of from 0.1 to 5 milliliters per hour at a distal end of the delivery line. The fluid infusion delivery system also employs a Y-site connector in the line for the intermittent introduction of a drug into the fluid delivered to the vein of a patient. In this case, an inlet branch line cf the connector may be provided with a check valve for separating a drug receiving chamber in the branch from a downstream chamber which is in communication with an IV catheter. A rubber septum may also be disposed over the inlet branch which is sized to permit piercing of a syringe needle therethrough for the infusion of a drug into the branch line under a pressure sufficient to pass through the check valve.

The invention also provides a method of infusing fluid into a vein which comprises the steps of placing an IV catheter in a vein, attaching a fluid delivery line to the catheter and continuously delivering fluid into the line under continuous positive pressure and restricting the fluid flow at a distal end of the line to a rate of from 0.1 to 5 millimeters per hour in order to maintain a positive pressure at the catheter or vein interface.

In accordance with the invention, micro-volumes of fluid are injected into the vein as opposed to the injection of macro-volumes which are currently in use. As a result, the incidence of complications due to the injection of fluids not required by the body are substantially reduced. In this respect, it has been found that so long as there is a positive pressure (almost no matter what the pressure is) at the opening of the catheter into a vein, a number of advantages occur. These advantages include the absence of backflow, the absence of diffusion of blood back into the catheter and the maintenance of the catheter in a patent state.

The fluid delivery apparatus also eliminates the need for Heparin since there is no need for this drug in an intermittent injection therapy to keep the line patent.

Further, the apparatus permits a patient to be truly ambulatory while his/her vein is readily available for medication injection without having to resort to the SASH procedure. Also, the apparatus prevents the migration of unwanted organisms, such as viruses, from the body into the apparatus which is exterior to the body and which may potentially become a source for nosicomial infection.

Other types of devices may also be connected with the infusion delivery system for the delivery of a bolus of medication into the delivery line to the IV catheter.

These and other objects and advantages of the invention will become more apparent from the following detailed description taken in conjunction with the accompanying drawings wherein:

FIG. 1 schematically illustrates a fluid infusion delivery system in accordance with the invention;

Figure 1:
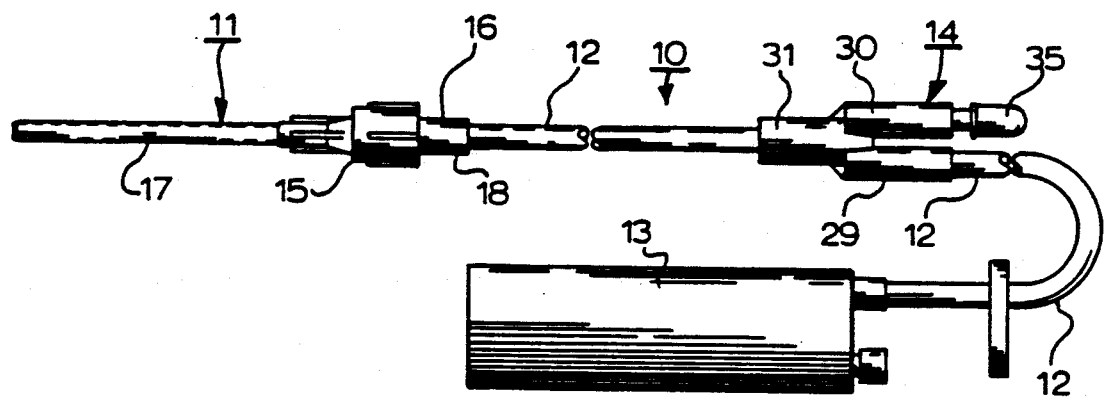

Referring to FIG. 1, the fluid infusion delivery system is constructed in the manner similar to that as described in U.S. Pat. No. 4,867,743. In this respect, the system 10 includes an IV catheter 11 for implantation in a vein of a patient (not shown), a fluid line 12 extending from the catheter 11 and a pump 13 connected to the line 12 for delivering fluid such as a saline solution into the line 12. A Y-site connector 14 is also provided in the line 12 for the periodic injection of a bolus of medication or drug. The IV catheter 11 includes a hub 15 having an inlet port 16 at one end and a hollow needle 17 mounted in the hub 15 in communication with the port 16. The needle 17 is sized for entry into a vein as is known. In this respect, the IV catheter 11 may be made of any conventional structure for the purpose of delivering fluid into an accessed vein.

The fluid line 12 extends from the hub 15 and is in communication with the inlet port 16 in order to deliver fluid thereto. In this respect, the fluid line 12 is provided with a luer connection 18 for interconnecting with the hub 15 in known manner. As indicated, the line 12 is interrupted by the Y-site connector 14 and has an inside diameter of from 0.015 inch to 0.025 inch, for example.

Figure 2:
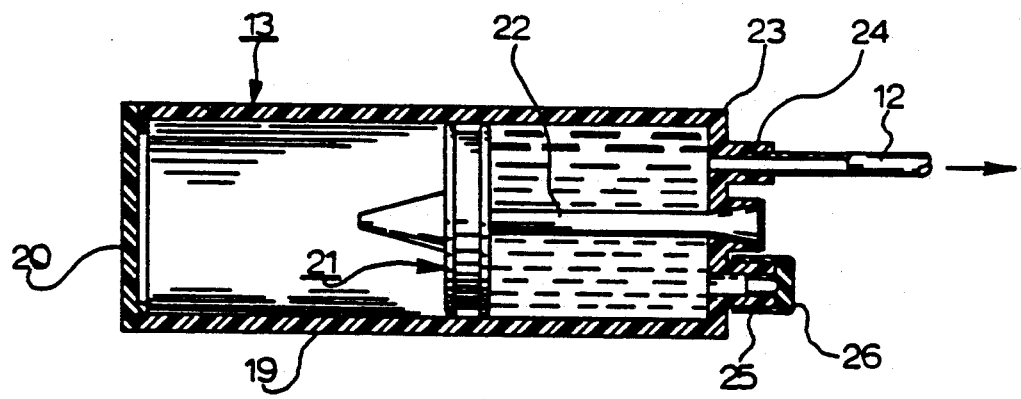
FIG. 2 illustrates a cross-sectional view of a pump for delivering fluid under a continuously applied pressure.

The pump 13 is connected to the fluid line 12 in order to deliver fluid into the line 12 under a continuously applied pressure. In this respect, the pump 13 is constructed so as to have mechanical energy storage properties in order to maintain a pressure on the fluid being delivered from the pump. For example, as shown in FIG. 2, the pump 13 may be constructed as described in U.S. Pat. No. 4,867,743 of an open-ended cylinder 19 having a closure cap 20 at one end to close off a chamber, a piston 21 slidably mounted in the cylinder 19 and a stretched elastomeric member 22 (or a spring or the like) to impose a continuous pressure on the fluid within the chamber between the piston 21 and the end wall 23 of the cylinder. The pump 13 is also constructed with an outlet 24 which receives the delivery line 12 to expel fluid at a pressure of from 1 to 15 psi as well as an inlet 25 in the end wall 23 for the injection of fluid. A cover 26 is also provided to close the inlet 25.

As indicated, the elastomeric member 22 is secured to and between the piston 21 and the end wall 23 of the cylinder 19.

Figure 3:
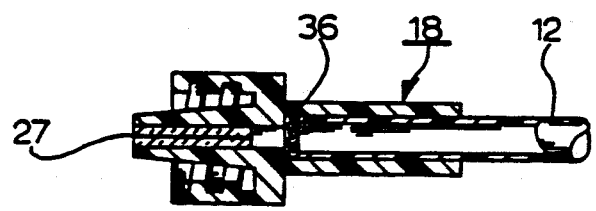
FIG. 3 illustrates a cross sectional view of a restrictor employed at the distal end of a fluid delivery line in accordance with the invention.

Referring to FIG. 3, a restrictor 27 is disposed in the line 12, for example, at the distal end of the line 12 relative to the flow of fluid, i.e. being disposed in the luer connection 18. This restrictor 27 is sized to produce a continual low flow rate at the outlet of the line 12 at a positive fluid pressure. For example, for the pressure range of the pump 13 noted above, the restrictor 27 is sized to produce a flow rate in a range of from 0.1 to 5 milliliters per hour and preferably in a range of from 0.1 to 1 milliliter per hour.

The restrictor 27 has an inside diameter of from 0.001 inch to 0.005 inch and a length of from ¼ inch to 1 inch. In the illustrated embodiment, the restrictor 17 is in the form of a capillary glass tube, for example having an inside diameter of 0.0016 inches and a length of 1 inch.

Figure 5:
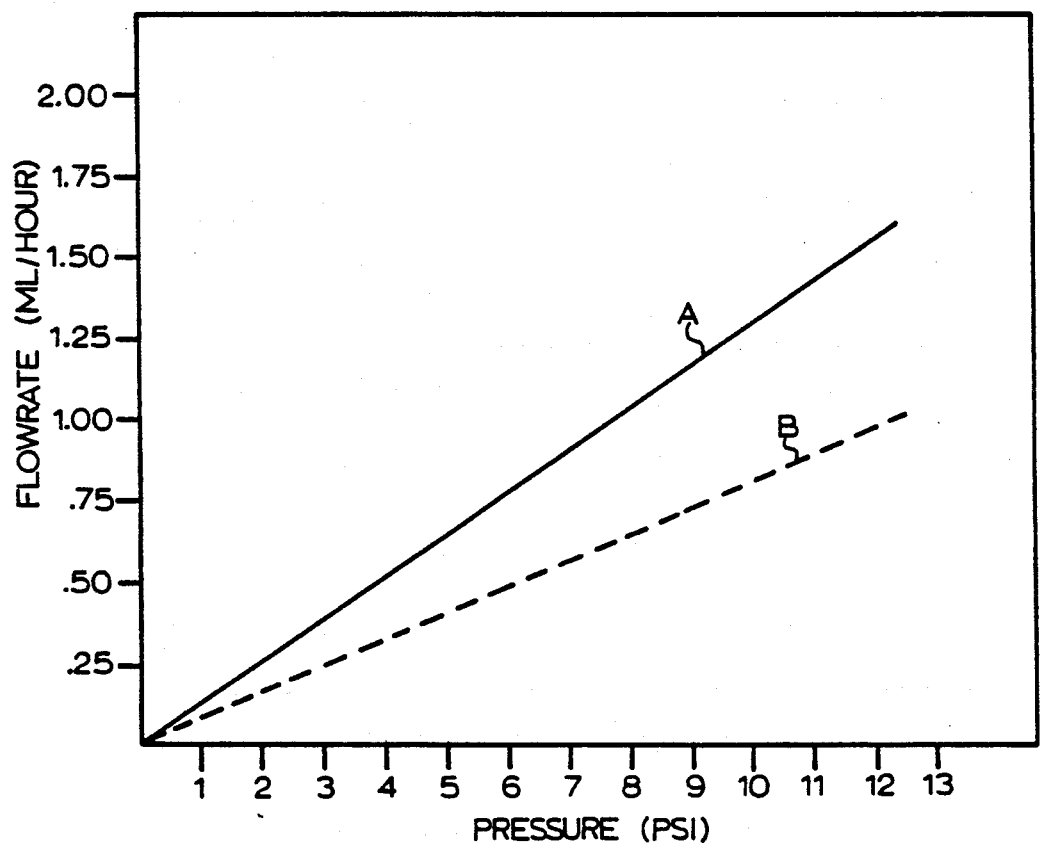
FIG. 5 graphically illustrates a flow rate versus pressure curve for different sized restrictors employed in accordance with the invention.

FIG. 5 graphically represents the flow rate and corresponding pressure for two glass capillary tubes of the same inside diameter, e.g. 0.0016 inches, and of different lengths for a given 5% dextrose solution. Line A for a tube having a length of 0.51 inches has a slope of 0.133 ml/psi while line B for a capillary tube of 0.742 inches has a slope of 0.093 ml/psi. As indicated, the flow rate is a function of the applied pressure for a given fluid, the inside diameter of the tube and the length of the tube. For example, the flow rate increases with increasing inside diameter and decreases with increasing length.

As shown in FIG. 3, a filter 28 is disposed upstream of the restrictor 27, for example, as described in U.S. Pat. No. 4,867,743 where the restrictor 27 is disposed elsewhere in the line 12 other than the distal end, for example, at the base of the pump 13, the filter 28 remains upstream of the restrictor 27 to prevent plugging.

Figure 4:
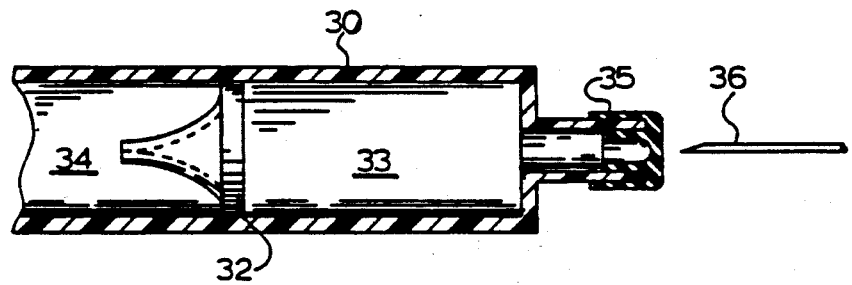
FIG. 4 illustrates a part cross-sectional view of an inlet branch of a Y-site connector constructed in accordance with the invention.

Referring to FIG. 1, the Y-site connector 14 is of generally conventional structure having one inlet branch 29 connected to the pump 13 for receiving fluid under pressure therefrom, a second inlet branch 30 for intermittently receiving a drug and an outlet branch 31 in communication with the hub 15 of the catheter 11 via the remainder of the line 12. In addition, as shown in FIG. 4, a check valve 32 is disposed within the second inlet branch 29 for dividing this branch into a first chamber 33 for receiving a drug and a second chamber 34 in communication with the line 12 to the IV catheter. A rubber septum 35 is also provided on the inlet branch 36 for sealing the chamber 33. This septum 35 is sized to permit piercing of a syringe needle 36 therethrough for infusion of a drug into the chamber 33 under a pressure sufficient to pass through the check valve 32.

Where a needle syringe device is used in combination with the rubber septum 35, the needle 36 should be small, for example of 25 gage or the septum 35 should be sized so that when the needle 36 is removed, fluid is released or injected to compensate for the needle volume or the drug is infused into a secondary port which allows the drug to escape into the main chamber with no change in volume of the chamber.

In order to infuse fluid into a vein, the needle 17 of an IV catheter II is initially placed in the vein at some point in time. Thereafter, the luer 18 of the fluid delivery line 12 is attached to the hub 15 of the catheter 11 and fluid is passed into the line 12 under a positive pressure by the pump 13 with the restrictor 27 maintaining a flow rate of from 0.1 to 5 millimeters per hour in order to maintain a positive pressure at the vein.

The invention thus provides a relatively simple system of maintaining a vein open without need for Heparin.

Further, the invention provides an infusion delivery system which prevents backflow into the line and, in particular, diffusion of blood back into the catheter implanted in a vein of a patient. The system thus allows a patient to be ambulatory while the patient's vein remains readily available for medication injection without having to resort to the SASH procedure.

Further, the invention provides a delivery system for infusing microvolumes of fluid into a vein to maintain the vein open.

What is claimed is:

1. A fluid infusion delivery system comprising
    an IV catheter including a hub having an inlet port at one end and a hollow catheter attached to said hub and in communication with said port, said catheter being sized for placement into the vein;
    a fluid line extending from said hub and being in communication with said inlet port to deliver fluid thereto;
    a pump connected to said fluid line for continuously delivering fluid into said line under a continuous positive pressure;
    a restrictor in said line for producing a low flow rate in a range of from 0.1 to 5 milliliters per hour at a distal end of said line; and
    a Y-site connector in said line having one inlet branch connected to said pump for receiving fluid therefrom, a second inlet branch for intermittently receiving a drug and an outlet branch communicating with said hub.

2. A system as set forth in claim 1 wherein said restrictor is a capillary glass tube.

3. A system as set forth in claim 2 wherein said capillary glass tube has an inside diameter in the range of 0.0016 inches.

4. A system as set forth in claim 1 wherein said fluid pressure is in a range of from 1 to 15 psi.

5. A system as set forth in claim 1 wherein said restrictor is disposed between said line and said hub.

6. A system as set forth in claim 1 wherein said flow rate is in the range of from 0.1 to 1 milliliter per hour.

7. A system as set forth in claim 1 which further includes a check valve dividing said second inlet branch into a first chamber for receiving a drug and a second chamber in communication with said hub and a rubber septum on said inlet branch for sealing said first chamber, said septum being sized to permit piercing of a syringe needle therethrough for infusion of a drug into said first chamber under a pressure sufficient to pass through said check valve.

8. A system as set forth in claim 1 wherein said restrictor is disposed downstream of said Y-site connector.

9. A fluid delivery apparatus for a fluid infusion delivery system comprising
    a fluid delivery line;
    a pump for delivering fluid under a positive fluid pressure into said delivery line;
    a Y-site connector in said line having one inlet branch connected to said pump for receiving fluid therefrom, an outlet branch for conveying fluid into said line receiving a drug for infusion into said line; and
    a restrictor in said delivery line for producing a continuous low flow rate of from 0.1 to 5 milliliters per hour at a distal end of said delivery line under said positive fluid pressure.

10. An apparatus as set forth in claim 9 wherein said flow rate is in the range of from 0.1 to 1 milliliter per hour.

11. An apparatus as set forth in claim 9 wherein said restrictor is a capillary glass tube.

12. An apparatus as set forth in claim 9 wherein said fluid pressure is in a range of from 1 to 15 psi.

13. An apparatus as set forth in claim 9 wherein said pump is sized for portability with an ambulatory patient.

14. A method of infusing fluid into a vein comprising the steps of
    placing an IV catheter in the vein;
    attaching a fluid delivery line to the catheter;
    continuously delivering fluid into said line under a positive pressure;
    restricting the flow in the line to a flow rate of from 0.1 to 5 milliliters per hour to maintain a positive pressure at the catheter or vein interface; and
    intermittently delivering a drug into said line for infusion into the vein.

15. A method as set forth in claim 14 wherein said flow rate is from 0.1 to 1 milliliters per hour.

* * * * *

UNITED STATES PATENT AND TRADEMARK OFFICE
CERTIFICATE OF CORRECTION

PATENT NO. : 5,059,174
DATED : Oct. 22, 1991
INVENTOR(S) : VINCENT L. VAILLANCOURT

It is certified that error appears in the above-identified patent and that said Letters Patent is hereby corrected as shown below:

Column 6, line 13 after "from" insert --a second inlet branch for receiving a drug and--

Line 14, after "line" (first occurrence) insert --and for--

Signed and Sealed this

Fourth Day of May, 1993

Attest:

MICHAEL K. KIRK

Attesting Officer

Acting Commissioner of Patents and Trademarks